United States Patent
Nakamura

(10) Patent No.: US 12,213,763 B2
(45) Date of Patent: Feb. 4, 2025

(54) OPTICAL COHERENCE TOMOGRAPHY (OCT) APPARATUS AND METHOD FOR CONTROLLING AN OPTICAL COHERENCE TOMOGRAPHY APPARATUS

(71) Applicant: NEC Corporation, Tokyo (JP)

(72) Inventor: Shigeru Nakamura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 192 days.

(21) Appl. No.: 17/908,994

(22) PCT Filed: Mar. 25, 2020

(86) PCT No.: PCT/JP2020/013452
§ 371 (c)(1),
(2) Date: Sep. 2, 2022

(87) PCT Pub. No.: WO2021/192117
PCT Pub. Date: Sep. 30, 2021

(65) Prior Publication Data
US 2023/0102868 A1    Mar. 30, 2023

(51) Int. Cl.
*G01B 9/02* (2022.01)
*A61B 3/10* (2006.01)
*A61B 5/00* (2006.01)

(52) U.S. Cl.
CPC ............ *A61B 5/0066* (2013.01); *A61B 3/102* (2013.01); *G01B 9/02* (2013.01)

(58) Field of Classification Search
CPC .... A61B 3/102; A61B 5/0066; G01B 9/02091
See application file for complete search history.

(56) References Cited

U.S. PATENT DOCUMENTS

2010/0097618 A1    4/2010    Haisch et al.
2011/0242487 A1    10/2011   Yuasa et al.
(Continued)

FOREIGN PATENT DOCUMENTS

CN    108375578 A    8/2018
JP    2004-252414 A  9/2004
(Continued)

OTHER PUBLICATIONS

International Search Report for PCT Application No. PCT/JP2020/013452, mailed on Jun. 30, 2020.
(Continued)

*Primary Examiner* — Maurice C Smith

(57) ABSTRACT

The optical interference tomographic imaging device is provided with: a wavelength sweeping laser light source; a branching unit that branches light emitted from the wavelength sweeping laser light source to object light and reference light; an irradiation unit that scans a predetermined range by irradiating different positions on the surface of the measurement target object with the object light outputted from the branching unit; a measurement unit that, after irradiation on the measurement target object, generates information about a change in the interference light intensity ratio between the reference light and the object light scattered from the measurement target object; and a control unit that, on the basis of the information about the change in the interference light intensity ratio generated by the measurement unit, acquires structure data in the depth direction of the measurement target object.

12 Claims, 10 Drawing Sheets

(56) References Cited

U.S. PATENT DOCUMENTS

| | | |
|---|---|---|
| 2013/0011035 A1 | 1/2013 | Shimoyama et al. |
| 2015/0048256 A1 | 2/2015 | Matsumura et al. |
| 2015/0363630 A1 | 12/2015 | Hogan |
| 2020/0309692 A1 | 10/2020 | Nakamura |

FOREIGN PATENT DOCUMENTS

| | | | | |
|---|---|---|---|---|
| JP | 2005-121602 A | | 5/2005 | |
| JP | 2010-133969 A | | 6/2010 | |
| JP | 2010-167253 A | | 8/2010 | |
| JP | 2011158309 A | * | 8/2011 | |
| JP | 2011-212202 A | | 10/2011 | |
| JP | 2017-211390 A | | 11/2017 | |
| JP | 2018115939 A | * | 7/2018 | |
| JP | 2019080804 A | * | 5/2019 | |
| KR | 20190081918 A | * | 7/2019 | |
| WO | WO-2019131298 A1 | * | 7/2019 | ......... G01B 9/02004 |

OTHER PUBLICATIONS

English translation of Written opinion for PCT Application No. PCT/JP2020/013452, mailed on Jun. 30, 2020.

* cited by examiner

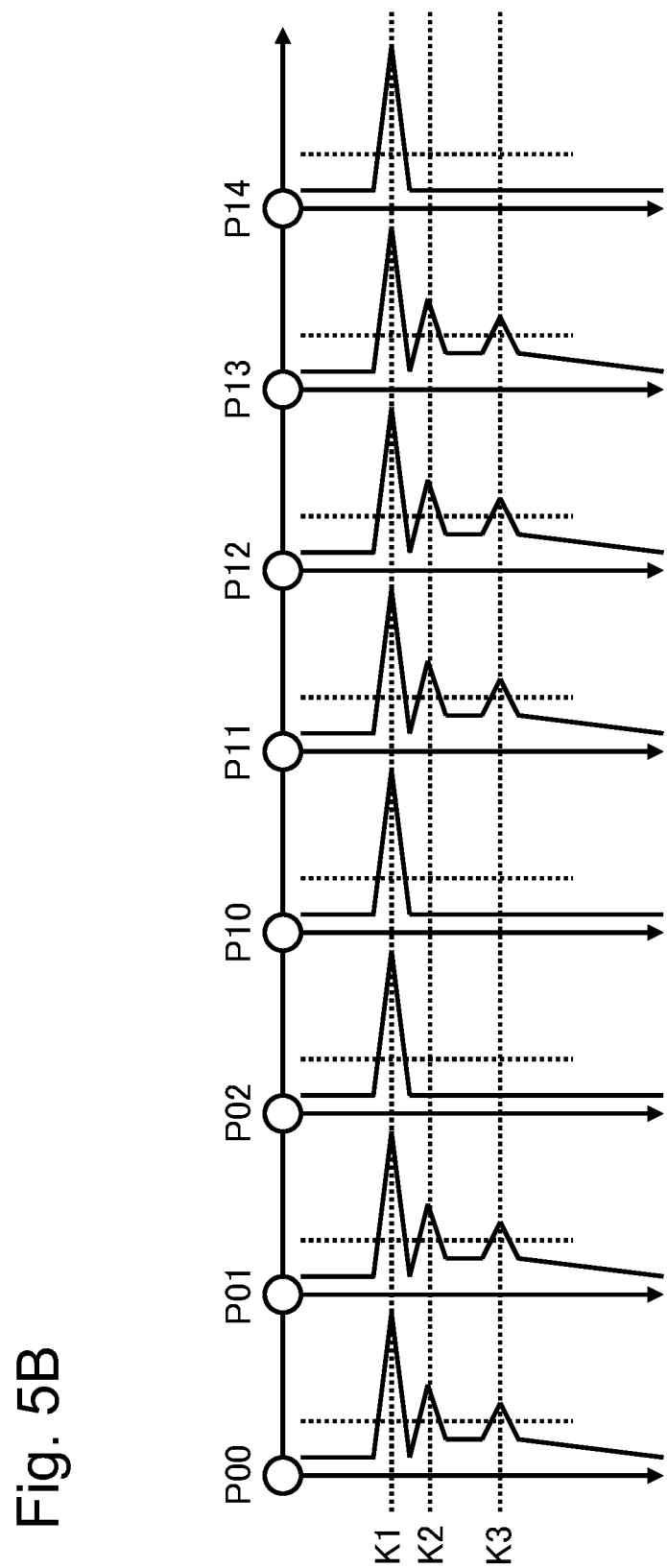

OPTICAL COHERENCE TOMOGRAPHY (OCT) APPARATUS AND METHOD FOR CONTROLLING AN OPTICAL COHERENCE TOMOGRAPHY APPARATUS

This application is a National Stage Entry of PCT/JP2020/013452 filed on Mar. 25, 2020, the contents of all of which are incorporated herein by reference, in their entirety.

TECHNICAL FIELD

This disclosure relates to an optical coherence tomography (OCT) apparatus.

BACKGROUND ART

As a technique for performing tomographic imaging in the vicinity of a surface of a measurement object, there is an optical coherence tomography (OCT) technique. In the OCT technology, tomographic imaging in the vicinity of the surface of the measurement object is performed using interference between scattered light (hereinafter, also referred to as "backscattered light") from the inside of the measurement object and reference light when the measurement object is irradiated with light beam. In recent years, the application of the OCT technology to medical diagnosis and industrial product inspection has been expanded.

In the OCT technology, a position in an optical axis direction, that is, a depth direction of a portion (light scattering point) in which object light is scattered in the measurement object is specified using interference between the object light emitted to the measurement object and scattered and the reference light. In many cases, the object light is not reflected by 100% only on the surface of the measurement object, but is scattered backward after being propagated to the inside of the measurement object to some extent. Therefore, it is possible to obtain structure data spatially resolved in the depth direction inside the measurement object. Examples of the OCT technology include a time domain (TD-OCT) method and a Fourier domain (FD-OCT) method, but the FD-OCT method is more promising in terms of high speed and high sensitivity. In the FD-OCT method, when object light and reference light are caused to interfere with each other, an interference light spectrum in a wide wavelength band is measured, and Fourier transform is performed on the measured interference light spectrum to obtain structure data in the depth direction. As a method for obtaining an interference light spectrum, there are a spectral domain (SD-OCT) method using a spectrometer and a swept source (SS-OCT) method using a light source that sweeps a wavelength.

Furthermore, by scanning an object light beam irradiation position of the measurement object in an in-plane direction perpendicular to the depth direction of the measurement object, it is possible to obtain tomographic structure data spatially resolved in the in-plane direction and spatially resolved in the depth direction. This makes it possible to obtain three-dimensional tomographic structure data of the measurement object. In order to irradiate different positions in the in-plane direction of the measurement object with object light beam, usually, the irradiation position of one object light beam is scanned by a galvano scanner or the like.

The OCT technology has been put into practical use as a tomographic imaging apparatus for the fundus in ophthalmic diagnosis, and also has been studied to be applied as a non-invasive tomographic imaging apparatus for various parts of a living body. For example, PTL 1 discloses a technique of reading a dermal fingerprint by utilizing OCT.

FIG. 7 illustrates a typical configuration of an SS-OCT optical coherence tomography (OCT) apparatus. A wavelength-swept light pulse is generated from a wavelength-swept laser light source 601. The light emitted from the wavelength-swept laser light source 601 is branched into object light R11 and reference light R21 at a branching and coupling device 604 via a circulator 603. The object light R11 passes through a fiber collimator 605 and an irradiation optical system 606 including a scanning mirror and a lens, and is emitted to a measurement object 620. Then, object light R31 scattered by the measurement object 620 returns to the branching and coupling device 604. On the other hand, the reference light R21 returns to the branching and coupling device 604 via a reference light mirror 608. Therefore, in the branching and coupling device 604, the object light R31 scattered from the measurement object 620 and reference light R41 reflected from the reference light mirror 608 interfere with each other, and interference light beams R51 and R61 are obtained. Therefore, intensity ratio between the interference light R51 and the interference light R61 is determined by the phase difference between the object light R31 and the reference light R41. The interference light R51 passes through the circulator 603 and is input to a two-input balanced optical receiver 602, and the interference light R61 is directly input to the two-input balanced optical receiver 602.

The intensity ratio between the interference light R51 and the interference light R61 changes with wavelength change of the light emitted from the wavelength-swept laser light source 601. As a result, photoelectric conversion output in the balanced optical receiver 602 can be measured as interference light spectrum. By measuring and Fourier-transforming the interference light spectrum, data indicating the intensity of the backscattered light (object light) at different positions in the depth direction (Z direction) is obtained (hereinafter, an operation of obtaining data indicating the intensity of the backscattered light (object light) in the depth direction (Z direction) at a certain position of the measurement object 620 is referred to as "A scan"), and this is performed by an A scan waveform generation unit 609.

In addition, on the basis of the control of the object light beam irradiation position setting unit 610, an A scan operation is repeatedly performed while the irradiation position of object light beam R11 is moved in a scanning line direction (X direction) by the irradiation optical system 606. By connecting A scan waveforms generated for each object light irradiation position, a map of two-dimensional intensity of backscattered light (object light) in the scanning line direction and the depth direction is obtained as tomographic structure data (hereinafter, an operation of repeatedly performing the A scan operation in the scanning line direction (X direction) and connecting the measurement results is referred to as "B scan").

Further, the B scan operation is repeatedly performed while the irradiation position of the object light beam R11 is moved not only in the scanning line direction but also in the direction (Y direction) perpendicular to the scanning line by the irradiation optical system 606, and the measurement results are connected, whereby three-dimensional tomographic structure data is obtained (hereinafter, an operation of repeatedly performing the B scan operation in the direction perpendicular to the scanning line (Y direction) and connecting the measurement results is referred to as "C scan"). The generation of the tomographic structure data based on the results of the B scan and the C scan is performed by a tomographic structure data generation unit 611.

When a living body is a measurement object, it is usually difficult to perform measurement while completely fixing the living body, and thus it is necessary to perform measurement in a short time. When the B scan and the C scan are performed, the object light beam irradiation position setting unit 610 controls the irradiation optical system 606 so that the object light beam irradiation positions are sequentially set as programmed in advance. An interval between the object light irradiation positions is 50 µm, and by repeating the irradiation 301 times, a range of 15 mm is irradiated. In a case where the measurement is performed in a wide range, it is difficult to speed up the measurement only by speeding up the object light beam scanning. Therefore, a configuration in which a plurality of object light beams is emitted is also known (PTL 2 and PTL 3).

CITATION LIST

Patent Literature

[PTL 1] US 2015/0363630 A
[PTL 2] JP 2010-167253 A
[PTL 3] WO 2019/131298 A

SUMMARY OF INVENTION

Technical Problem

Since the area of the measurement object varies, when the measurement object is scanned while the object light beam irradiation position is set as programmed in advance, a region other than the measurement object may be irradiated with the object light beam. When the measurement object is a living body or the like and the measurement needs to be performed in a short time, the time for irradiating the region other than the measurement object with the object light beam is wasted.

For example, FIG. 8 schematically illustrates a relationship between the measurement object and the object light beam irradiation position when the area of the measurement object is large and small in a case where a fingertip is the measurement object and a dermal fingerprint is read. When the measurement object is large, the object light beam irradiation position is often on the measurement object, but when the measurement object is small, the object light beam irradiation position is often not on the measurement object.

An object of this disclosure is to provide an optical coherence tomography (OCT) apparatus capable of performing high-speed measurement while minimizing the time during which a region other than a measurement object is irradiated with object light beam.

Solution to Problem

In order to achieve the above object, an optical coherence tomography (OCT) apparatus according to this disclosure includes:
a wavelength-swept laser light source;
a branching unit that branches light emitted from the wavelength-swept laser light source into object light and reference light;
an irradiation unit that irradiates different positions on a surface of a measurement object with the object light output from the branching unit to scan a predetermined range;
a measurement unit that generates information on a change in an intensity ratio between interference light beams generated from the object light emitted to the measurement object and then scattered from the measurement object and the reference light; and
a control unit that acquires structure data in a depth direction of the measurement object, based on the information on the change in the intensity ratio between the interference light beams generated by the measurement unit, and
further includes
an object light irradiation position setting unit that determines whether the measurement object is irradiated with the object light based on the information generated by the measurement unit and that sets an irradiation position of the object light controlled by the irradiation unit.

An optical coherence tomography (OCT) apparatus according to this disclosure includes:
a wavelength-swept laser light source;
a first branching unit that branches light emitted from the wavelength-swept laser light source into a plurality of light beams;
a second branching unit that branches the plurality of light beams output from the first branching unit into object light and reference light, respectively;
an irradiation unit that irradiates different positions on a surface of the measurement object with the plurality of the object light beams output from the second branching unit to scan a predetermined range;
a measurement unit that generates information on a change in an intensity ratio between interference light beams generated from the object light emitted to the measurement object and then scattered from the measurement object and the reference light; and
a control unit that acquires structure data in a depth direction of the measurement object, based on the information on the change in the intensity ratio between the interference light beams generated by the measurement unit, and
further includes
an object light irradiation position setting unit that determines whether the measurement object is irradiated with the object light based on the information generated by the measurement unit and that sets an irradiation position of the object light controlled by the irradiation unit.

A method for controlling an optical coherence tomography (OCT) apparatus according to this disclosure, the optical coherence tomography (OCT) apparatus including:
a wavelength-swept laser light source; a branching unit that branches light emitted from the wavelength-swept laser light source into object light and reference light; an irradiation unit that irradiates different positions on a surface of a measurement object with the object light output from the branching unit to scan a predetermined range; a measurement unit that generates information on a change in an intensity ratio between interference light beams generated from the object light emitted to the measurement object and then scattered from the measurement object and the reference light; and a control unit that acquires structure data in a depth direction of the measurement object, based on the information on the change in the intensity ratio between the interference light beams generated by the measurement unit, the method including:

determining whether the measurement object is irradiated with the object light based on the information generated by the measurement unit, and setting an irradiation position of the object light controlled by the irradiation unit.

Advantageous Effects of Invention

In the optical coherence tomography (OCT) apparatus according to this disclosure, by providing a mechanism for setting an object light irradiation position while determining whether object light irradiates a measurement object, it is possible to speed up measurement while minimizing the time during which a region other than the measurement object is irradiated with object light beam.

BRIEF DESCRIPTION OF DRAWINGS

FIG. 5B is an explanatory diagram illustrating a method of detecting a B scan end point of the optical coherence tomography (OCT) apparatus according to the first example embodiment of this disclosure.

EXAMPLE EMBODIMENT

Figure 1:
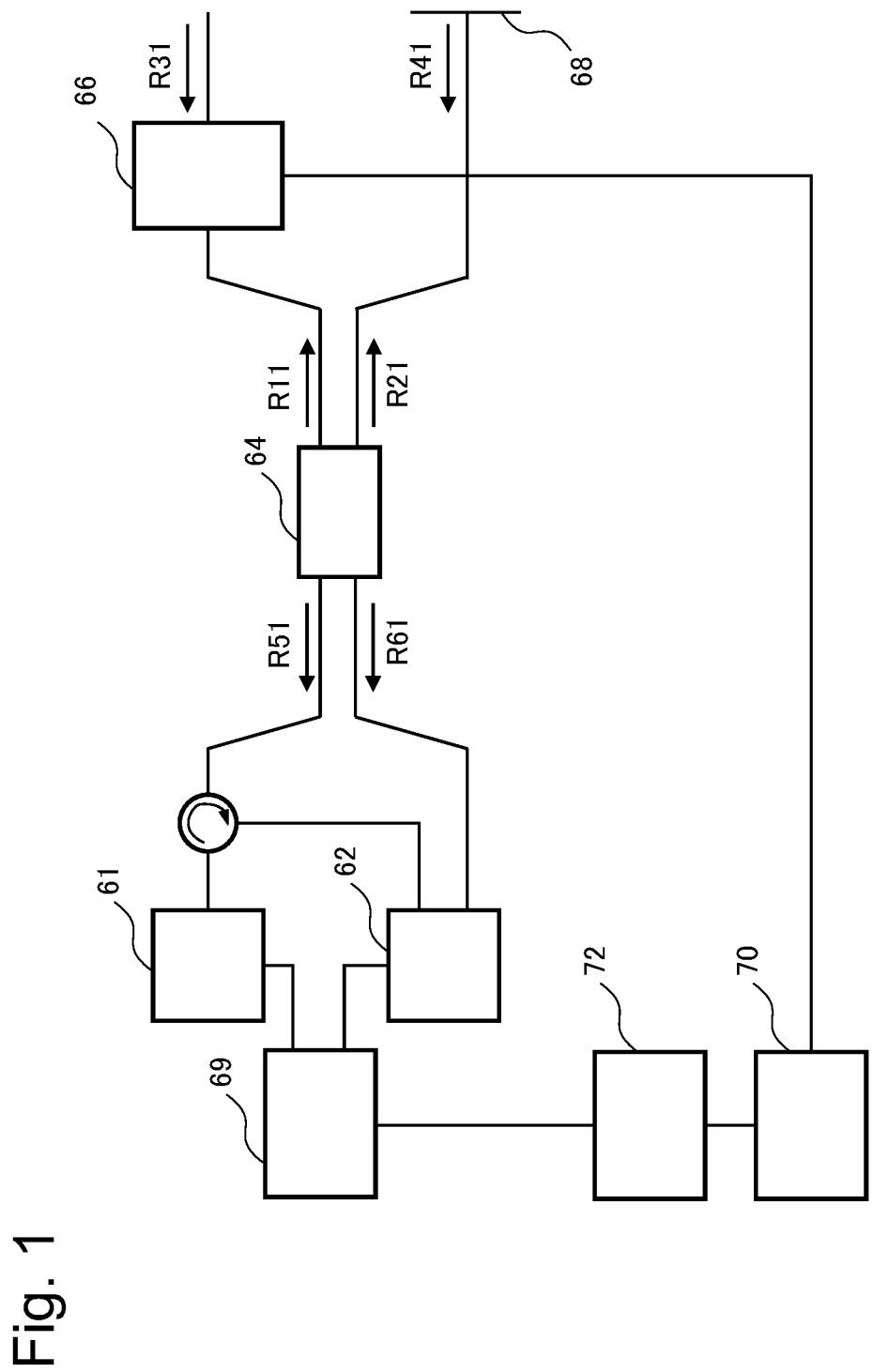
FIG. 1 is a block diagram for explaining an optical coherence tomography (OCT) apparatus according to an example embodiment of a superordinate concept of this disclosure.

Hereinafter, example embodiments of this disclosure will be described with reference to the drawings.
[Example Embodiment of Superordinate Concept]
Before describing specific example embodiments, an optical coherence tomography (OCT) apparatus according to an example embodiment of a superordinate concept of this disclosure will be described. FIG. 1 is a block diagram illustrating an example of an optical coherence tomography (OCT) apparatus according to the example embodiment of the superordinate concept of this disclosure.

The optical coherence tomography (OCT) apparatus 60 of FIG. 1 includes a wavelength-swept laser light source 61, a circulator 63 and an optical branching and coupling device 64 as an example of a branching unit, an irradiation optical system 66 and a reference light mirror 68 as an example of an irradiation unit, a balanced optical receiver 62 as an example of a measurement unit, an A scan waveform generation unit 69, a tomographic image generation unit 70, and a B scan end point determination unit 72 as an example of a control unit, and the like.

The light incident from the wavelength-swept laser light source 61 passes through the circulator 63 and is branched into object light R11 and reference light R21 by the optical branching and coupling device 64. The object light R11 output from the optical branching and coupling device 64 passes through the irradiation optical system 66, and is emitted to the measurement object and scanned. More specifically, the irradiation optical system 66 scans a certain range by irradiating one plane of the measurement object with the object light beam under the control of the scanning cycle and speed of the measurement object.

The reference light R21 output from the optical branching and coupling device 64 is reflected by the reference light mirror 68 and returns to the optical branching and coupling device 64.

In the optical branching and coupling device 64, object light R31 scattered from the measurement object and reference light R41 reflected from the reference light mirror 68 interfere with each other, and interference light R51 and interference light R61 are obtained.

The interference light R51 is input to the balanced optical receiver 62 through the circulator 63, and the interference light R61 is directly input to the balanced optical receiver 62. Information regarding a change in the intensity ratio between the interference light R51 and the interference light R61 is input from the balanced optical receiver 62 to the A scan waveform generation unit 69. The A scan waveform generation unit 69 generates interference light spectrum data based on information on wavelength change of the emission light from the wavelength-swept laser light source 61 and information on intensity difference between the interference light R51 and the interference light R61 from the balanced optical receiver 62. Further, an A scan operation is repeatedly performed while moving the object light beam irradiation position by the irradiation optical system 66, and the measurement results are connected, thereby obtaining a map of the two-dimensional intensity of the backscattered light (object light) in a scanning line direction and a depth direction as B scan tomographic structure data.

In this example embodiment, the B scan end point determination unit 72 determines an end point of the B scan. The determination of the end point of the B scan is achieved by a method such as determining whether the object light beam is irradiated on the measurement object from the characteristics of an A scan waveform. When the end point of the B scan is detected, the current B scan is ended, and the next B scan is started. By connecting the measurement results obtained by repeatedly performing the B scan operation while moving the irradiation position of the object light beam R11 in the scanning line direction and a direction perpendicular to the scanning line, three-dimensional tomographic structure data of the measurement object is generated (C scan).

According to this example embodiment, by adaptively setting the object light beam irradiation position with respect to an area of the measurement object, it is possible to increase the speed and resolution of the measurement. Hereinafter, a more specific example embodiment will be described.

First Example Embodiment

Figure 2:
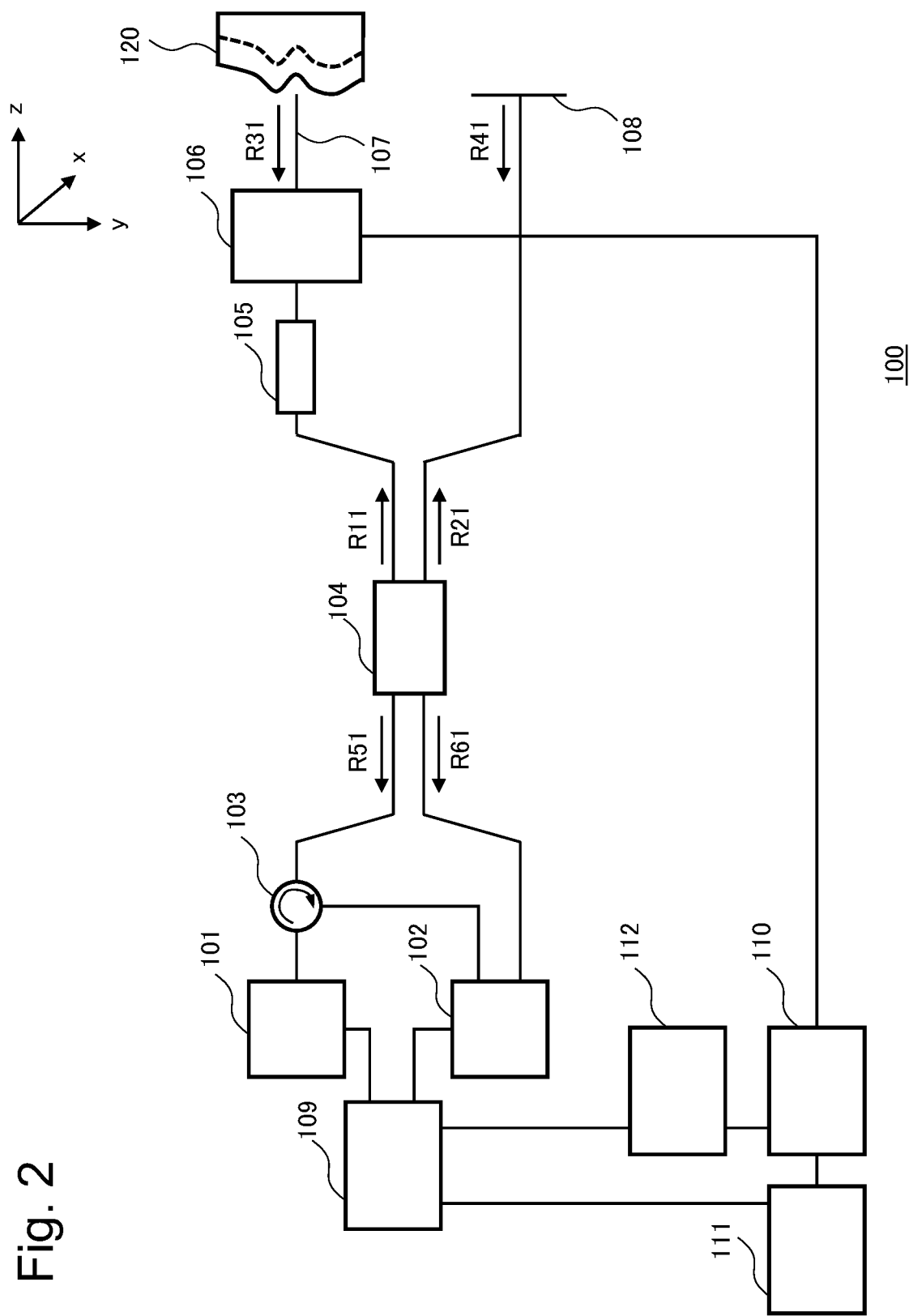
FIG. 2 is a block diagram illustrating an example of an optical coherence tomography (OCT) apparatus according to a first example embodiment of this disclosure.

Next, an optical coherence tomography (OCT) apparatus according to a first example embodiment of this disclosure will be described with reference to the drawings. FIG. 2 is a configuration diagram illustrating a first example embodiment of the optical coherence tomography (OCT) apparatus according to this disclosure. As illustrated in FIG. 2, the optical coherence tomography (OCT) apparatus 100 includes a wavelength-swept laser light source 101, a circulator 103, an optical branching and coupling device 104, a fiber collimator 105, an irradiation optical system 106, a reference light mirror 108, a balanced optical receiver 102, an A scan waveform generation unit 109, a tomographic image generation unit 110, an object light beam irradiation position setting unit 111, a B scan end point determination unit 112, and the like.

The wavelength-swept laser light source 101 generates a wavelength-swept light pulse. Specifically, the wavelength-swept laser light source 101 generates light pulses whose wavelength increases from 1250 nm to 1350 nm for a duration of 10 μs. The wavelength-swept laser light source 101 repeatedly generates the light pulse at 50 kHz every 20 μs.

The light emitted from the wavelength-swept laser light source 101 is branched into object light R11 and reference light R21 by the optical branching and coupling device 104.

The object light R11 output from the optical branching and coupling device 104 passes through the fiber collimator 105 and the irradiation optical system 106, and is emitted to the measurement object 120 and scanned.

The irradiation optical system 106 includes, for example, a scanning mirror and a lens, and irradiates different positions on an X-Y plane of the measurement object 120 with object light beam 107 to scan a certain range.

The object light beam 107 emitted to the measurement object 120 is scattered backward (in a direction opposite to the irradiation direction of the object light beam) from the measurement object 120. Then, object light (backscattered light) R31 scattered from the measurement object 120 returns to the optical branching and coupling device 104 via the irradiation optical system 106 and the fiber collimator 105.

Reference light R21 output from the optical branching and coupling device 104 is reflected by the reference light mirror 108 and returns to the optical branching and coupling device 104.

Therefore, in the optical branching and coupling device 104, the object light R31 scattered from the measurement object 120 and reference light R41 reflected from the reference light mirror 108 interfere with each other, and interference light beams R51 and R61 are obtained.

The interference light R51 passes through the circulator 103 and input to the associated balanced optical receiver 102, and the interference light R61 is directly input to the associated balanced optical receiver 102. Then, information regarding a change in the intensity ratio between the interference light R51 and the interference light R61 is input from the balanced optical receiver 102 to the A scan waveform generation unit 109. Note that the balanced optical receiver 102 is an optical receiver in which two photodiodes are connected in series and the connection is an output (differential output).

Interference between object light having a wavelength λ and a wave number k (=2π/λ) and reference light is considered. In a case where an optical path length from when the reference light is branched at the optical branching and coupling device 104 to when the reference light is reflected by the reference light mirror 108 and returns to the optical branching and coupling device 104 is $L_R$, and an optical path length from when the object light is branched at the optical branching and coupling device 104 to when the object light is backscattered at one light scattering point of the measurement object 120 and returns to the optical branching and coupling device 104 is $L_S=L_R+z_0$, the object light R31 and the reference light R41 interfering at the optical branching and coupling device 104 interfere with each other at a phase difference of $kz_0+\varphi$. Here, φ is a constant that does not depend on k or $z_0$. When amplitude of the object light R31 interfering at the optical branching and coupling device 104 is denoted by $E_S$ and amplitude of the reference light R41 is denoted by $E_R$, the intensity difference between the interference light R51 and the interference light R61 represented by $$I(k) \propto E_S \cdot E_R \cdot \cos(kz_0+\phi) \qquad \text{[Equation 1]}$$

is photoelectrically converted by the balanced optical receiver 102.

The A scan waveform generation unit 109 generates interference light spectrum data on the basis of the information regarding the wavelength change of the emission light from the wavelength-swept laser light source 101 and the information regarding the intensity difference between the interference light R51 and the interference light R61 from the balanced optical receiver 102, and performs Fourier transform thereof. When there is backscattered light at the light scattering point position $z_0$ inside the measurement object, modulation with a period $2\pi/z_0$ appears in interference light spectrum data I(k) obtained by measuring from the wave number $k_0-\Delta k/2$ to $k_0+\Delta k/2$. The amplitude J(z) of the Fourier transform of I(k) is represented by $$J(z) = |\int I(k) e^{ikz} dk| \propto \delta(z-z_0)+\delta(z+z_0) \qquad \text{[Equation 2]}$$

and $z=z_0$ (and $z=-z_0$) shows a delta-functional peak. The position of the light scattering point is one in the case of a mirror, but usually, the object light irradiated to the measurement object is sequentially backscattered while being propagated while being attenuated to the inside to some extent, and the light scattering point of the object light is distributed in a range from the surface to a certain depth. In a case where the light scattering points are distributed from $z_0-\Delta z$ to $z_0+\Delta z$ in the depth direction, modulation from the period $2\pi/(z_0-\Delta z)$ to $2\pi/(z_0+\Delta z)$ appears in an overlapping manner in the interference light spectrum, and this forms an A scan waveform.

The output of the A scan waveform generation unit 109 is transferred to the B scan end point determination unit 112, and after it is determined whether it is the end point of the B scan, the object light beam of the irradiation optical system 106 is controlled on the basis of setting signal from the object light beam irradiation position setting unit 111 according to the determination result. By repeatedly performing the A scan operation while moving the irradiation position of the object light beam R11 in the scanning line direction (X direction) by the irradiation optical system 106 and connecting the measurement results, a map of the two-dimensional intensity of the backscattered light (object light) in the scanning line direction and the depth direction is obtained as B scan tomographic structure data.

Further, the object light beam irradiation position setting unit 111 generates three-dimensional tomographic structure data in the X, Y, and Z directions by connecting measurement results obtained by repeatedly performing the B scan operation while moving the irradiation position of the object light beam R11 in the scanning line direction and the direction perpendicular to the scanning line (C scan).

Figure 3A:
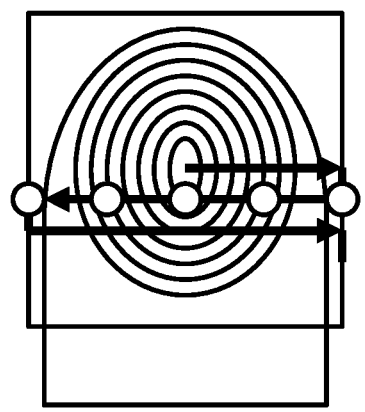
FIG. 3 is a view illustrating an example of an object light beam scanning pattern using an irradiation optical system in the optical coherence tomography (OCT) apparatus according to the first example embodiment of this disclosure.
Figure 3B:
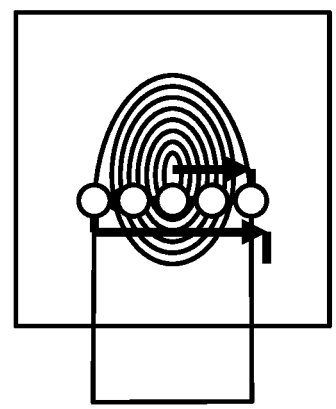

The setting of the object light beam irradiation position is adaptively performed according to the area of the measurement object. FIG. 3 illustrate examples of setting of the object light beam irradiation position. FIG. 3 illustrate examples in which a fingertip is used as a measurement object in order to read a subcutaneous dermal fingerprint from tomographic structure data. When the area of the measurement object is large, the object light beam irradiation position is set such that an irradiation position interval is increased to irradiate the entire width of the measurement object as illustrated in FIG. 3A. When the area of the measurement object is small, the object light beam irradiation position is set such that the irradiation position interval is reduced as illustrated in FIG. 3B and the entire width of the measurement object is irradiated, measurement with higher spatial resolution becomes possible in a region where the measurement object exists, and object light beam irradiation point to a region where the measurement object does not exist is minimized, and measurement in a short time becomes possible.

Figure 4:
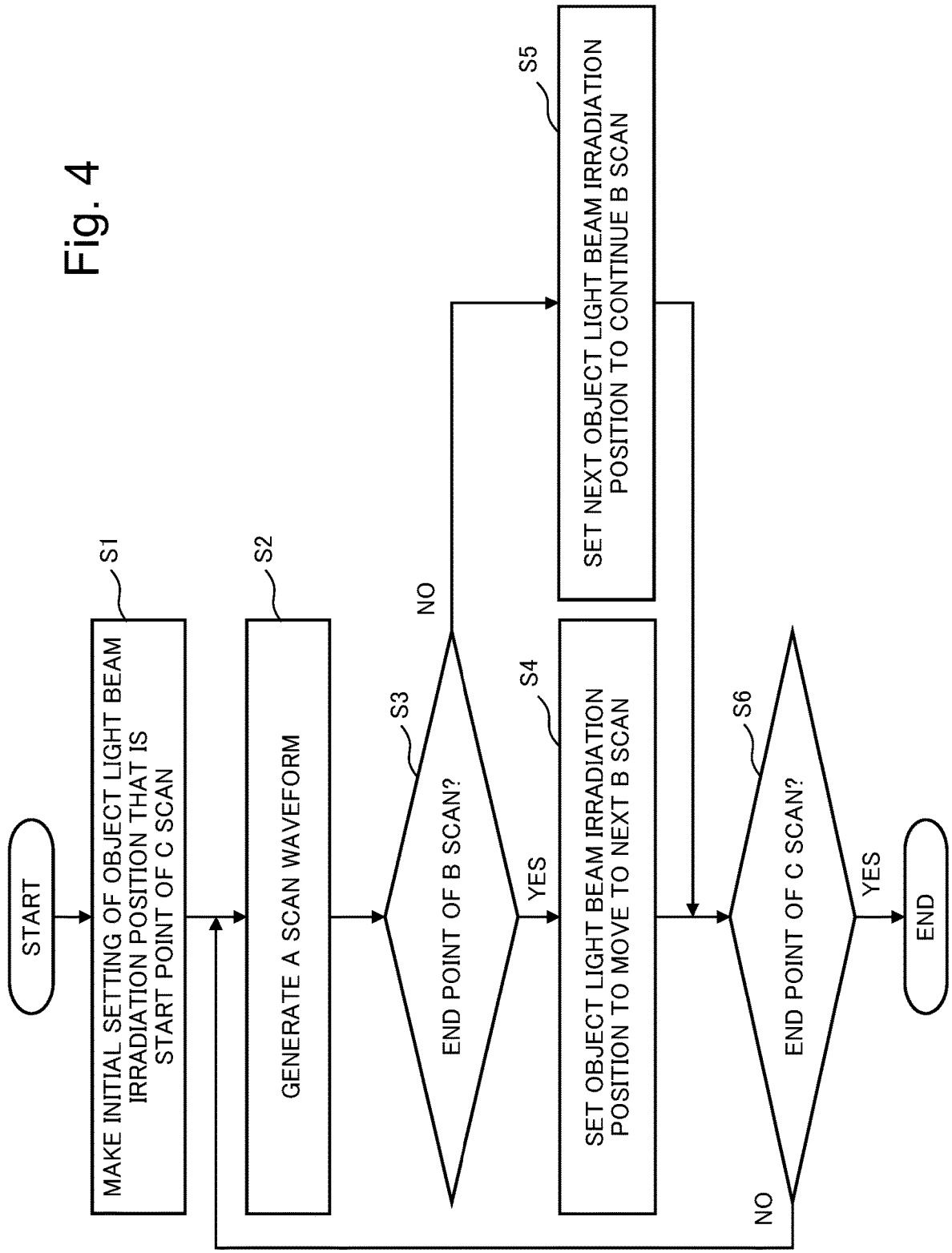
FIG. 4 is a flowchart illustrating an operation procedure of the optical coherence tomography (OCT) apparatus according to the first example embodiment of this disclosure.

FIG. 4 is a flowchart of a measurement procedure. The measurement procedure includes: step S1 of initially setting an object light beam irradiation position to be a start point of the C scan; step S2 of irradiating a predetermined position of the measurement object with the object light beam and generating an A scan waveform from the result of interference between backscattered light and reference light; step S3 of determining whether the position is an end point of the B scan; step S4 of setting the object light beam irradiation position to a next B scan position when the position is the end point of the B scan; step S5 of setting the object light beam irradiation position so as to continue the B scan when the position is not the end point of the B scan; and step S6 of determining whether the position is the end point of the C scan.

First, in the step S1, an object light beam irradiation position to be a start point of C scan is initially set. Here, a center of a range in which the object light beam can be irradiated is set as a start point. Next, in the step S2, an A scan waveform is generated from a result of interference between the backscattered light of the object light beam emitted at the set position and the reference light. Next, in the step S3, it is determined whether the object light beam is irradiated on the measurement object from the characteristics of the generated A scan waveform. In a case where the object light beam is irradiated on the measurement object, it is determined that it is not the end point of the B scan, and in a case where the object light beam is not irradiated on the measurement object, it is determined that it is the end point of the B scan. Next, in a case where the end point of the B scan is not been detected, in the step S4, next object light beam irradiation position is set so as to continue the B scan. In a case where the end point of the B scan is detected, next object light beam irradiation position is set such that the B scan is ended and next B scan is started in the step S5. Next, in the step S6, it is determined whether the set next object light beam irradiation position is an end point of the C scan.

Figure 5A:
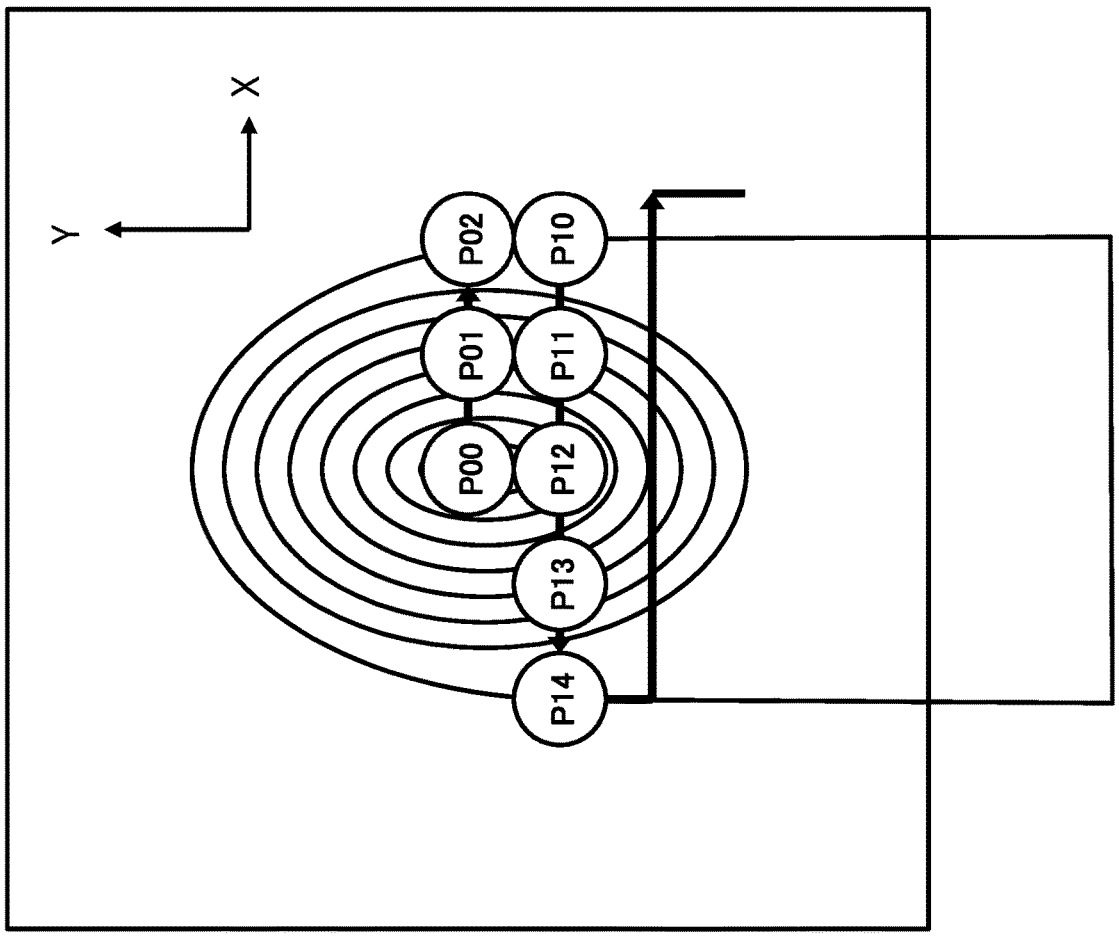
FIG. 5A is an explanatory diagram illustrating a method of detecting a B scan end point of the optical coherence tomography (OCT) apparatus according to the first example embodiment of this disclosure.

A procedure of B scan end point determination using the A scan waveform will be described with reference to FIGS. 5A and 5B. An object light beam irradiation position order in FIG. 5A is in a form of a so-called raster scan. The initial setting of the irradiation position of the object light beam is P00, and the A scan waveform is generated for each irradiation position while sequentially irradiating a position P01 and a position P02. The initial setting value of interval between the irradiation positions is 50 µm, and the moving direction of the irradiation positions is the direction of x.

When the fingertip as the measurement object is pressed against a glass plate, a peak K1 indicating light reflection from the glass plate, a peak K2 indicating light reflection from the epidermis of the finger, and a peak K3 indicating light reflection from the dermis inside the finger appear in the generated A scan waveform. This A scan waveform generation is performed at 50 kHz, and is performed in real time for each object light beam irradiation position. Therefore, whether the object light beam is emitted to the measurement object can be determined in real time by the presence or absence of the peak K2 or the peak K3 in the A scan waveform.

Here, the epidermis of the finger as the measurement object is an example of the surface of the measurement object, and the dermis inside the finger is an example of the structure existing in the depth direction from the surface of the measurement object. The glass plate is an example of a transparent member located between the irradiation optical system 106 and the measurement object.

The measurement object is irradiated with the object light beam at the position P00 and the position P01, but the measurement object is not irradiated with the object light beam at the position P02, so that the B scan end point is detected at this time point. The A scan waveform data at the position P00, the position P01, and the position P02 is also transferred to the tomographic image generation unit 110, and a B scan image Q0 is generated by connecting the A scan waveforms.

When the B scan end point is detected at the position P02, the next object light beam irradiation position is set at the position P10, and the interval between the object light beam irradiation positions is also reset according to the area of the measurement object. When the measurement object is smaller than the measurable range, the object light beam irradiation interval is set to a value smaller than the initial setting, and is reset to 30 µm here. The A scan waveform is generated for each irradiation position while sequentially irradiating the position P11, the position P12, the position P13, and the position P14. The measurement object is irradiated with the object light beam at the position P10, the position P11, the position P12, and the position P13, but the measurement object is not irradiated with the object light beam at the position P14. At this point, the B scan end point is detected. A B scan image Q1 is generated in the tomographic image generation unit 110 from the A scan waveforms at the position P10, the position P11, the position P12, the position P13, and the position P14.

By connecting the B scan images obtained by repeating the above procedure, 3D tomographic data as a result of the C scan is generated.

Figure 5C:
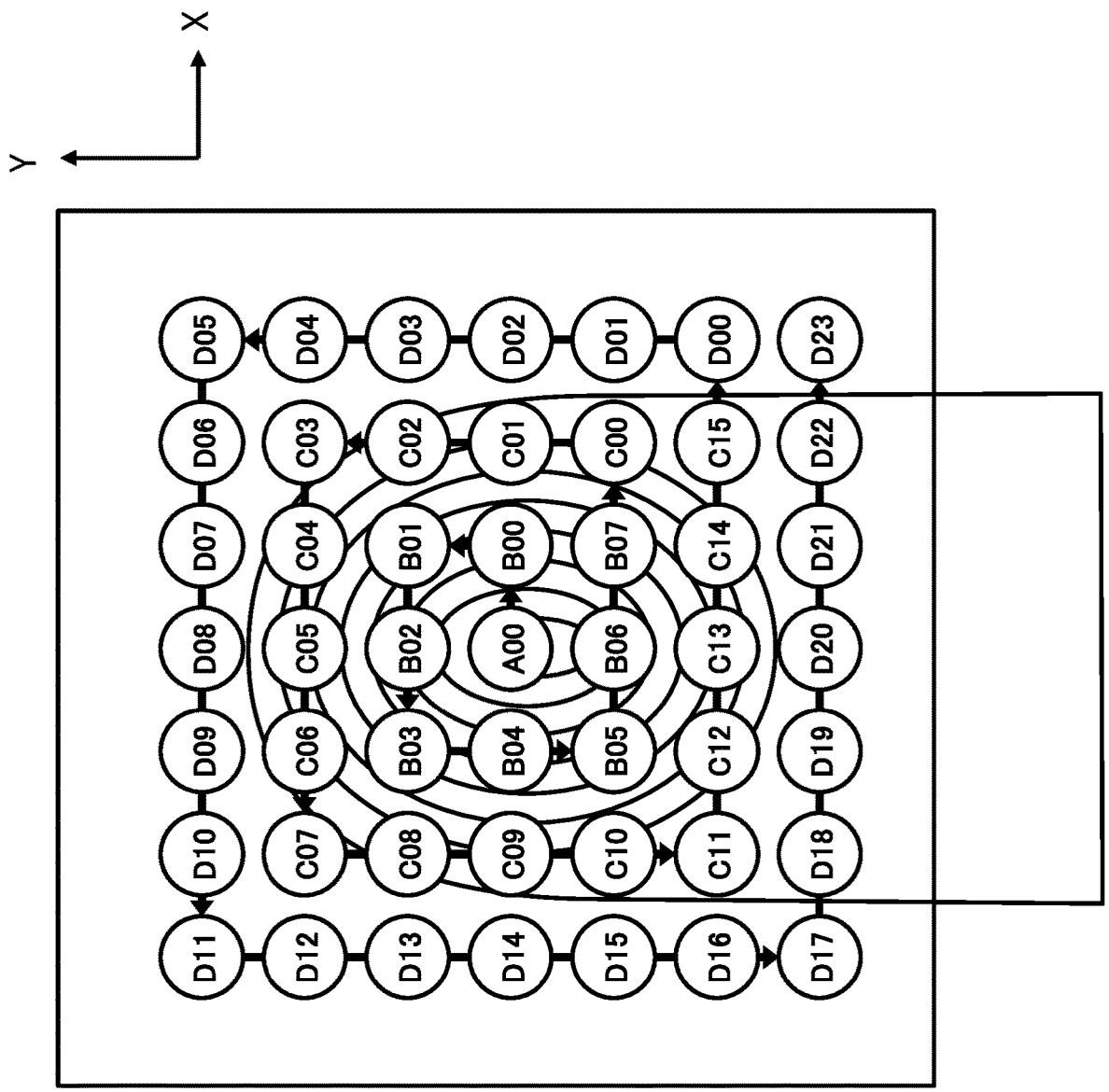
FIG. 5C is an explanatory diagram illustrating another example of the method of detecting the B scan end point of the optical coherence tomography (OCT) apparatus according to the first example embodiment of this disclosure.

Note that the object light beam irradiation position order is not limited to the so-called raster scan described above. FIG. 5C illustrates an example in a case of so-called vector scanning. The object light beam irradiation is started from A00, and is set to sequentially perform the irradiation to the outside. Therefore, the object light beam irradiation position order is set such that irradiation from B00 to B07 is performed next, irradiation from C00 to C15 is performed next, and irradiation from D00 to D23 is performed next. At the time of irradiation with the object light beams of the three sides from D00 to D05, from D06 to D11, and from D12 to D17 among D00 to D23, the measurement object was not detected. Therefore, it is found that there is no need to further irradiate the outside, and the end point of the scan can be detected. As a result, the irradiation is performed from D00 to D23, and the object light beam irradiation is completed.

(Effects of Example Embodiment)

With the configuration described above, by adaptively setting the object light beam irradiation position with respect to the area of the measurement object, it is possible to increase the speed and resolution of the measurement.

The reason is that, by repeatedly performing the A scan operation and connecting the measurement results, while obtaining a map of two-dimensional intensity of backscattered light (object light) in the scanning line direction and the depth direction as the B scan tomographic structure data, the B scan end point determination unit 112 determines the end point of the B scan, and when the end point of the B scan is detected, the current B scan is ended and the next B scan is started. Further, this is because the determination of the end point of the B scan is achieved by determining whether the object light beam is irradiated on the measurement object from the characteristics of the generated A scan waveform.

Second Example Embodiment

Figure 6:
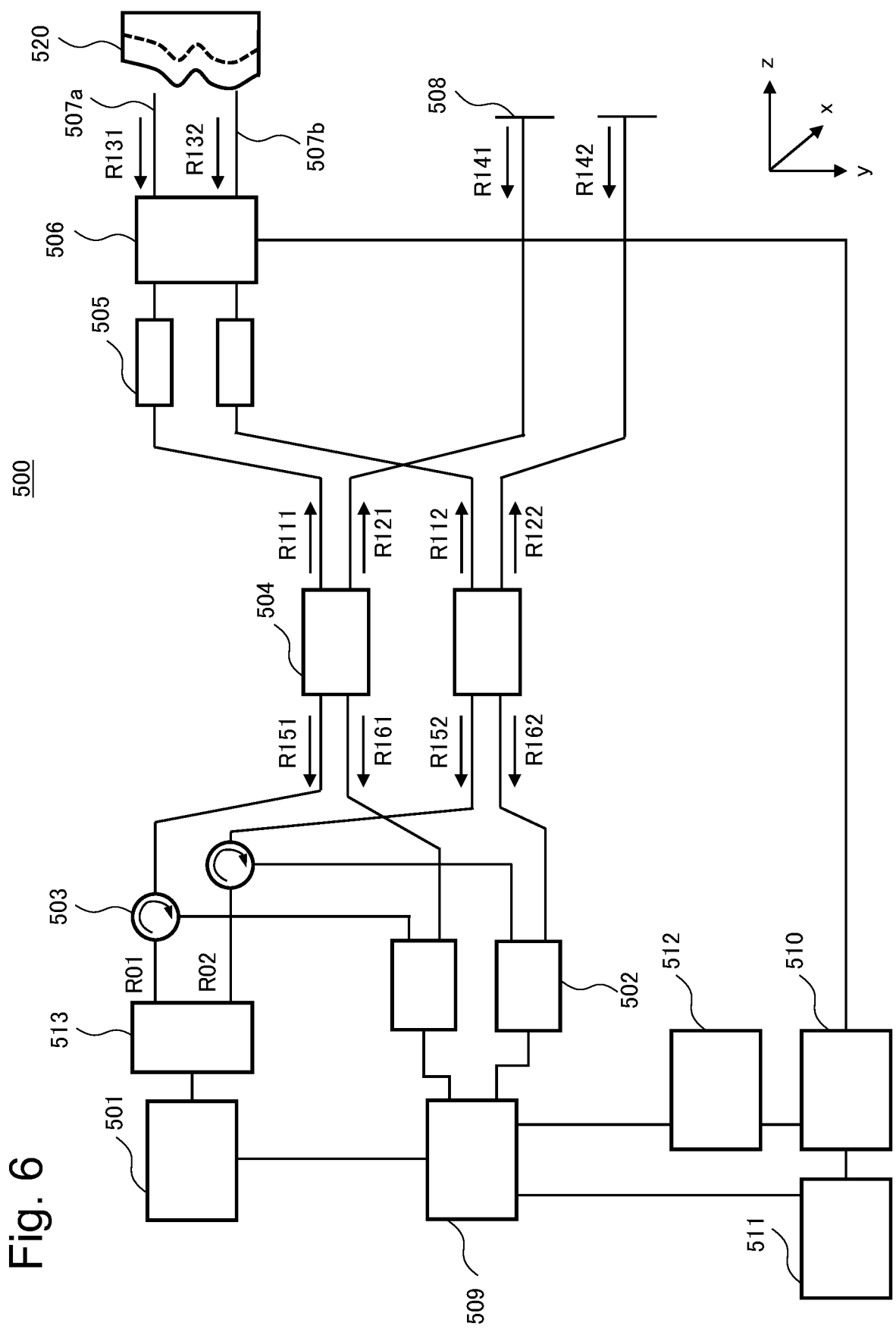
FIG. 6 is a block diagram illustrating an example of an optical coherence tomography (OCT) apparatus according to a second example embodiment of this disclosure.
Figure 7:
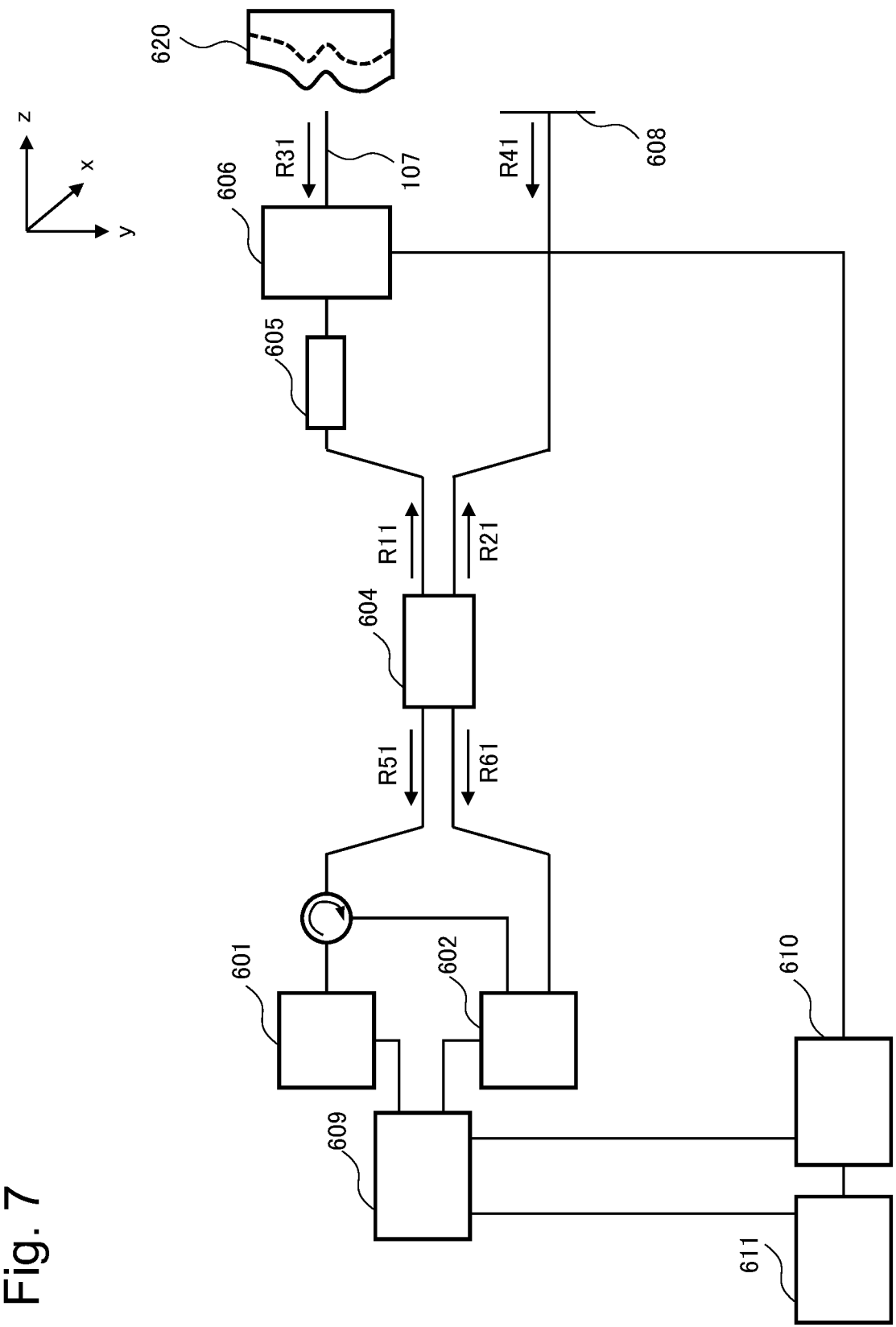
FIG. 7 is a view illustrating an example of a related optical coherence tomography (OCT) apparatus.
Figure 8:
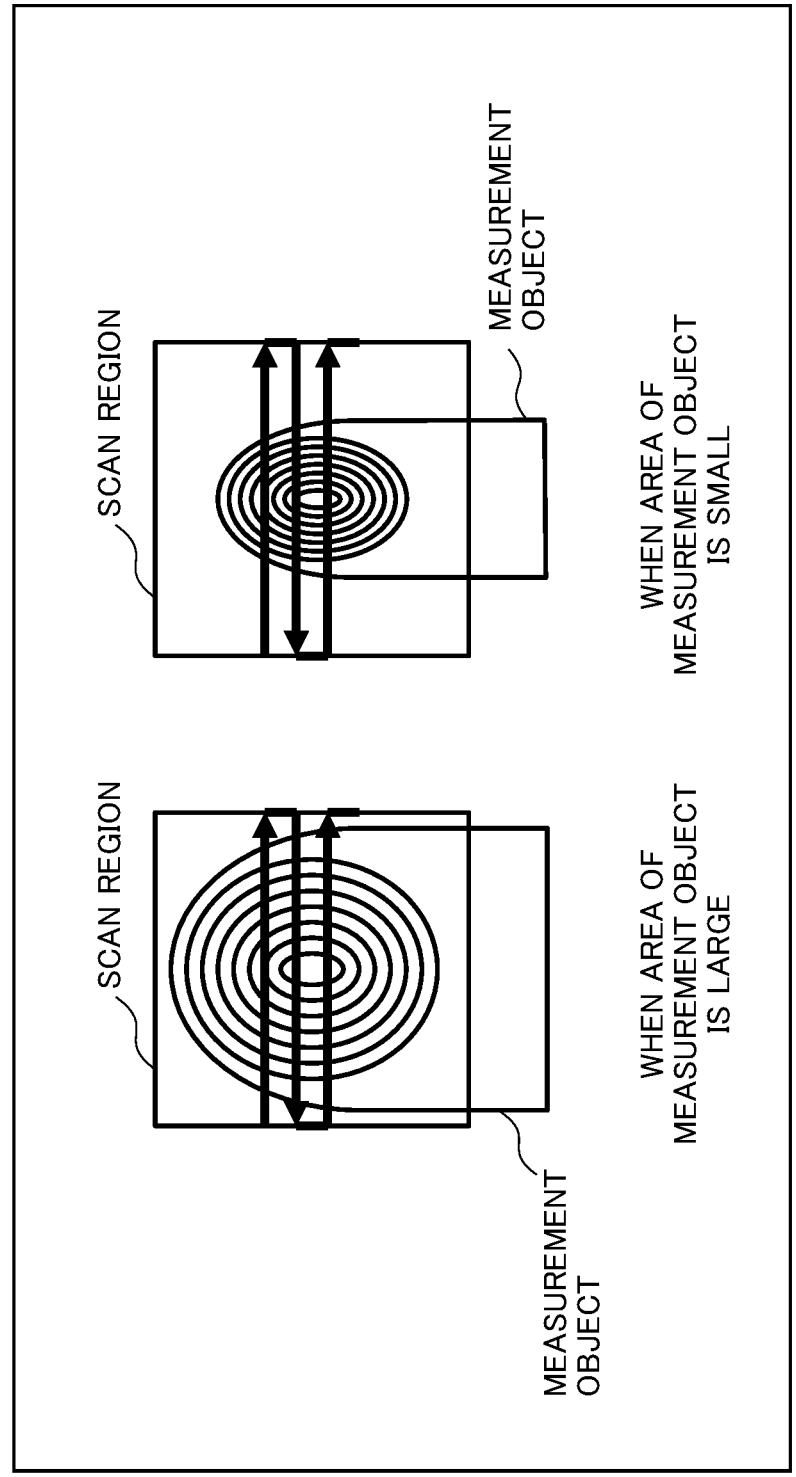
FIG. 8 is a view illustrating an example of an object light beam scanning pattern using an irradiation optical system in a related optical coherence tomography (OCT) apparatus.

Next, an optical coherence tomography (OCT) apparatus according to a second example embodiment of this disclosure will be described with reference to the drawings. This example embodiment relates to an optical coherence tomography (OCT) apparatus that irradiates a measurement object with a plurality of measurement light beams and connects the measurement results to obtain a map of two-dimensional intensity of backscattered light (object light) in a scanning line direction and a depth direction as B scan tomographic structure data. FIG. 6 is a configuration diagram illustrating the second example embodiment of the optical coherence tomography (OCT) apparatus according to this disclosure. As illustrated in FIG. 6, an optical coherence tomography (OCT) apparatus 500 includes a wavelength-swept laser light source 501, an optical branching device 513, a plurality of circulators 503, a plurality of optical branching and coupling devices 504, a plurality of fiber collimators 505, an irradiation optical system 506, a reference light mirror 508, a plurality of balanced optical receivers 502, an A scan waveform generation unit 509, a tomographic image generation unit 510, an object light beam irradiation position setting unit 511, a B scan end point determination unit 512, and the like. Note that the number of the optical branching and coupling devices 504, the number of the fiber collimators 505, and the number of the balanced optical receivers 502 included in the optical coherence tomography (OCT) apparatus 500 may be determined according to the number of light beams emitted from the wavelength-swept laser light source 501 branched in the optical branching device 513, and are not limited to the illustrated numbers.

The wavelength-swept laser light source 501 generates a wavelength-swept light pulse. Specifically, the wavelength-swept laser light source 501 generates light pulses whose wavelength increases from 1250 nm to 1350 nm for a duration of 10 μs. The wavelength-swept laser light source 101 repeatedly generates the light pulse at 50 kHz every 20 μs.

The light emitted from the wavelength-swept laser light source 501 is branched into a plurality of light beams R01 and R02 by the optical branching device 513, and then branched into object light beams R111 and R112 and reference light beams R121 and R122 by the plurality of optical branching and coupling devices 504 via the plurality of circulators 503.

The plurality of object light beams R111 and R112 output from the optical branching and coupling device 504 are emitted to the measurement object 520 through the fiber collimator 505 and the irradiation optical system 506 and scanned. More specifically, the irradiation optical system 506 includes, for example, a scanning mirror and a lens, and irradiates different positions on an X-Y plane of the measurement object 520 with the plurality of object light beams 507a and 507b to scan a certain range.

The object light beams 507a and 507b emitted to the measurement object 520 are scattered backward (in a direction opposite to the irradiation direction of the object light beam) from the measurement object 520. Then, the object light beams (backscattered light) R131 and R132 scattered from the measurement object 520 return to the optical branching and coupling device 504 via the irradiation optical system 506 and the fiber collimator 505.

The plurality of reference light beams R121 and R122 output from the optical branching and coupling device 504 are reflected by the reference light mirror 508 and return to the optical branching and coupling device 504.

Therefore, in the optical branching and coupling device 504, the object light R131 scattered from the measurement object 520 and reference light R141 reflected from the reference light mirror 508 interfere with each other, and interference light beams R151 and R161 are obtained. Similarly, in the optical branching and coupling device 504, the object light R132 scattered from the measurement object 520 and the reference light R142 reflected from the reference light mirror 508 interfere with each other, and interference light beams R152 and R162 are obtained. Therefore, the intensity ratio between the interference light beams R151 and R152 and the interference light beams R161 and R162 is determined by the phase difference between the object light beams R131 and R132 and the reference light beams R141 and R142.

The interference light beams R151 and R152 pass through the circulator 103 and input to the associated balanced optical receiver 502, and the interference light beams R161 and R162 are directly input to the associated balanced optical receiver 502. Then, information on the change in the intensity ratio between the interference light R151 and the interference light R161 and information on the change in the intensity ratio between the interference light R152 and the interference light R162 are input from the balanced optical receiver 502 to the A scan waveform generation unit 509. Note that the balanced optical receiver 502 is an optical receiver in which two photodiodes are connected in series and the connection is an output (differential output).

In addition, the optical path length of the object light and the optical path length of the reference light from when the object light R111 and the reference light R121 are branched by the optical branching and coupling device 504 to when the backscattered light R131 of the object light and the return light R141 of the reference light are coupled again are substantially equal. When there is a large difference in the optical path lengths, frequency difference (wavelength difference) between the object light R131 and the reference light R141 interfering at the optical branching and coupling device 504 becomes larger than the band of the balanced optical receiver 502, and it becomes impossible to detect the intensity ratio between the interference light R151 and the interference light R161 reflecting the phase difference between the object light R131 and the reference light R141. In addition, the optical path length of the object light and the optical path length of the reference light from when the object light R112 and the reference light R122 are branched by the optical branching and coupling device 504 to when the backscattered light R132 of the object light and the return light R142 of the reference light are coupled again are substantially equal. When there is a large difference in the optical path lengths, frequency difference (wavelength difference) between the object light R132 and the reference light R142 interfering at the optical branching and coupling device 504 becomes larger than the band of the balanced optical receiver 502, and it becomes impossible to detect the intensity ratio between the interference light R151 and the interference light R161 reflecting the phase difference between the object light R131 and the reference light R141.

The A scan waveform generation unit 509 generates an A scan waveform based on the information on the wavelength change of the emission light from the wavelength-swept laser light source 501 and the information on the change in the intensity ratio between the interference light beams R151 and R161. Similarly, the A scan waveform generation unit 509 generates an interference light spectrum on the basis of the information regarding the wavelength change of the emission light from the wavelength-swept laser light source 501 and the information regarding the change in the intensity ratio between the interference light beams R152 and R162.

The output of the A scan waveform generation unit 509 is transferred to the B scan end point determination unit 512, and after it is determined whether it is the end point of the B scan, the object light beam of the irradiation optical system 506 is controlled on the basis of setting signal from the object light beam irradiation position setting unit 511 according to the determination result. By repeatedly performing the A scan operation while moving the irradiation position of the object light beam R111 in the scanning line direction (X direction) by the irradiation optical system 506 and connecting the measurement results, a map of the two-dimensional intensity of the backscattered light (object light) in the scanning line direction and the depth direction is obtained as B scan tomographic structure data.

Further, the tomographic image generation unit 510 generates three-dimensional tomographic structure data in the X, Y, and Z directions by connecting measurement results obtained by repeatedly performing the B scan operation while moving the irradiation position of the object light beam R111 in the scanning line direction and the direction perpendicular to the scanning line (C scan).

(Effects of Example Embodiment)

With the configuration described above, similarly to the first example embodiment, by adaptively setting the object light beam irradiation position with respect to the area of the measurement object, it is possible to increase the speed and resolution of the measurement.

The reason is that, by repeatedly performing the A scan operation and connecting the measurement results, while obtaining a map of two-dimensional intensity of backscattered light (object light) in the scanning line direction and the depth direction as the B scan tomographic structure data, the B scan end point determination unit 112 determines the end point of the B scan, and when the end point of the B scan is detected, the current B scan is ended and the next B scan is started. Further, this is because the determination of the end point of the B scan is achieved by determining whether the object light beam is irradiated on the measurement object from the characteristics of the generated A scan waveform.

Furthermore, even in an optical coherence tomography (OCT) apparatus that obtains a map of two-dimensional intensity of backscattered light (object light) in a scanning line direction and a depth direction as B scan tomographic structure data by irradiating a measurement object with a plurality of measurement light beams and connecting the measurement results, it is possible to increase measurement speed and resolution by adaptively setting an object light beam irradiation position with respect to an area of the measurement object.

While the invention has been particularly shown and described with reference to exemplary embodiments thereof, the invention is not limited to these embodiments. For example, in the above-described example embodiment, it has been assumed that this disclosure is applied to an SS-OCT optical coherence tomography (OCT) apparatus, but this disclosure can also be applied to an optical coherence tomography (OCT) apparatus of another system, for example, a TD-OCT optical coherence tomography (OCT) apparatus or an SD-OCT optical coherence tomography (OCT) apparatus. It will be understood by those of ordinary skill in the art that various changes in form and details may be made therein without departing from the spirit and scope of this disclosure as defined by the claims.

Some or all of the above example embodiments may be described as the following Supplementary Notes, but are not limited to the following.

(Supplementary Note 1) An optical coherence tomography (OCT) apparatus, including:
 a wavelength-swept laser light source;
 a branching unit that branches light emitted from the wavelength-swept laser light source into object light and reference light;
 an irradiation unit that irradiates different positions on a surface of a measurement object with the object light output from the branching unit to scan a predetermined range;
 a measurement unit that generates information on a change in an intensity ratio between interference light beams generated from the object light emitted to the measurement object and then scattered from the measurement object and the reference light; and
 a control unit that acquires structure data in a depth direction of the measurement object, based on the information on the change in the intensity ratio between the interference light beams generated by the measurement unit, and
 further including
 an object light irradiation position setting unit that determines whether the measurement object is irradiated with the object light based on the information generated by the measurement unit and that sets an irradiation position of the object light controlled by the irradiation unit.

(Supplementary Note 2) An optical coherence tomography (OCT) apparatus, including:
 a wavelength-swept laser light source;
 a first branching unit that branches light emitted from the wavelength-swept laser light source into a plurality of light beams;
 a second branching unit that branches the plurality of light beams output from the first branching unit into object light and reference light, respectively;
 an irradiation unit that irradiates different positions on a surface of the measurement object with the plurality of the object light beams output from the second branching unit to scan a predetermined range;
 a measurement unit that generates information on a change in an intensity ratio between interference light beams generated from the object light emitted to the measurement object and then scattered from the measurement object and the reference light; and a control unit that acquires structure data in a depth direction of the measurement object, based on the information on the change in the intensity ratio between the interference light beams generated by the measurement unit, and further including an object light irradiation position setting unit that determines whether the measurement object is irradiated with the object light based on the information generated by the measurement unit and that sets an irradiation position of the object light controlled by the irradiation unit.

(Supplementary Note 3) The optical coherence tomography (OCT) apparatus according to the Supplementary Note 1 or 2, wherein the object light irradiation position setting unit sets a center of an irradiatable range as a start point with respect to initial setting of an irradiation position where the measurement object is irradiated with the object light.

(Supplementary Note 4) The optical coherence tomography (OCT) apparatus according to any one of the Supplementary Notes 1 to 3, wherein the object light irradiation position setting unit changes the irradiation position of the object light in a direction substantially perpendicular to a scanning direction of the object light when detecting an end point of the scanning direction of the object light.

(Supplementary Note 5) The optical coherence tomography (OCT) apparatus according to any one of the Supplementary Notes 1 to 4, wherein the object light irradiation position setting unit determines an end point in a direction in which the object light is scanned by determining whether the object light is emitted onto the measurement object based on the information on the change in the intensity ratio of the interference light between the interference light and the reference light generated by the irradiation unit irradiating the object light.

(Supplementary Note 6) The optical coherence tomography (OCT) apparatus according to the Supplementary Note 5, wherein the object light irradiation position setting unit determines whether the object light is emitted onto the measurement object based on information caused by the object light scattered from the surface of the measurement object among the pieces of information on the change in the intensity ratio between the interference light beams generated by the irradiation unit irradiating the object light.

(Supplementary Note 7) The optical coherence tomography (OCT) apparatus according to the Supplementary Note 6, wherein the object light irradiation position setting unit determines whether the object light is emitted onto the measurement object based on information caused by the object light scattered from a structure existing in the depth direction from the surface of the measurement object among the pieces of information related to the change in the intensity ratio between the interference light beams generated by the irradiation unit irradiating the object light.

(Supplementary Note 8) The optical coherence tomography (OCT) apparatus according to the Supplementary Note 6 or 7, wherein the object light irradiation position setting unit determines whether the object light is emitted onto the measurement object in consideration of information caused by the object light scattered from a transparent member located between the irradiation unit and the measurement object among the pieces of information related to the change in the intensity ratio between the interference light beams generated by the irradiation unit irradiating the object light.

(Supplementary Note 9) A method for controlling an optical coherence tomography (OCT) apparatus, the optical coherence tomography (OCT) apparatus including: a wavelength-swept laser light source; a branching unit that branches light emitted from the wavelength-swept laser light source into object light and reference light; an irradiation unit that irradiates different positions on a surface of a measurement object with the object light output from the branching unit to scan a predetermined range; a measurement unit that generates information on a change in an intensity ratio between interference light beams generated from the object light emitted to the measurement object and then scattered from the measurement object and the reference light; and a control unit that acquires structure data in a depth direction of the measurement object, based on the information on the change in the intensity ratio between the interference light beams generated by the measurement unit, the method including:

determining whether the measurement object is irradiated with the object light based on the information generated by the measurement unit, and setting an irradiation position of the object light controlled by the irradiation unit.

(Supplementary Note 10) The method for controlling an optical coherence tomography (OCT) apparatus according to the Supplementary Note 9, further including setting a center of an irradiatable range as a start point with respect to initial setting of an irradiation position where the measurement object is irradiated with the object light.

(Supplementary Note 11) The method for controlling an optical coherence tomography (OCT) apparatus according to the Supplementary Note 9 or 10, further including changing the irradiation position of the object light in a direction substantially perpendicular to a scanning direction of the object light when an end point of the scanning direction of the object light is detected.

(Supplementary Note 12) The method for controlling an optical coherence tomography (OCT) apparatus according to any one of the Supplementary Notes 9 to 11, further including determining an end point in the scanning direction of the object light, by determining whether the object light is emitted onto the measurement object based on the information on the change in the intensity ratio between the interference light beams generated by the irradiation unit irradiating the object light and generated by the reference light.

REFERENCE SIGNS LIST 100, 500 optical coherence tomography (OCT) apparatus
101, 501 wavelength-swept laser light source
102, 502 balanced optical receiver
103, 503 circulator
104, 504 optical branching and coupling device
105, 505 fiber collimator
106, 506 irradiation optical system 107, 507a, 507b object light beam
108, 508 reference light mirror
109, 509 A scan waveform generation unit
110, 510 tomographic image generation unit
111, 511 object light beam irradiation position setting unit
112, 512 B scan end point determination unit
120, 520 measurement object
513 optical branching device

What is claimed is:

1. An optical coherence tomography (OCT) apparatus, comprising:
    a wavelength-swept laser light source;
    an optical branching device configured to branch light emitted from the wavelength-swept laser light source into object light and reference light; and
    an irradiation optical system configured to irradiate different positions on a surface of a measurement object with the object light output from the optical branching device to scan a predetermined range,
    wherein the optical coherence tomography (OCT) apparatus is configured to perform:
        generating information on a change in an intensity ratio between interference light beams generated from the object light emitted to the measurement object and then scattered from the measurement object and the reference light;
        acquiring structure data in a depth direction of the measurement object, based on the information on the change in the intensity ratio between the interference light beams, and
        determining whether the measurement object is irradiated with the object light based on the generated information and setting an irradiation position of the object light controlled by the irradiation optical system.

2. An optical coherence tomography (OCT) apparatus, comprising:
    a wavelength-swept laser light source;
    a first optical branching device configured to branch light emitted from the wavelength-swept laser light source into a plurality of light beams;
    a second optical branching device configured to branch the plurality of light beams output from the first optical branching device into object light and reference light, respectively; and
    an irradiation optical system configured to irradiate different positions on a surface of the measurement object with the plurality of the object light beams output from the second optical branching device to scan a predetermined range,
    wherein the optical coherence tomography (OCT) apparatus is configured to perform:
        generating information on a change in an intensity ratio between interference light beams generated from the object light emitted to the measurement object and then scattered from the measurement object and the reference light;
        acquiring structure data in a depth direction of the measurement object, based on the information on the change in the intensity ratio between the interference light beams generated by the measurement means, and further comprising
        an object light irradiation position setting means configured to determine determining whether the measurement object is irradiated with the object light based on the generated information and setting an irradiation position of the object light controlled by irradiation optical system.

3. The optical coherence tomography (OCT) apparatus according to claim 1, wherein
    the optical coherence tomography (OCT) apparatus is configured to perform:
        setting a center of an irradiatable range as a start point with respect to initial setting of an irradiation position where the measurement object is irradiated with the object light.

4. The optical coherence tomography (OCT) apparatus according to any one of claim 1, wherein
    the optical coherence tomography (OCT) apparatus is configured to perform:
        changing the irradiation position of the object light in a direction substantially perpendicular to a scanning direction of the object light when detecting an end point of the scanning direction of the object light.

5. The optical coherence tomography (OCT) apparatus according to claim 1, wherein
    the optical coherence tomography (OCT) apparatus is configured to perform:
        determining an end point in a direction in which the object light is scanned by determining whether the object light is emitted onto the measurement object based on the information on the change in the intensity ratio between the interference light beams generated by the irradiation optical system irradiating the object light.

6. The optical coherence tomography (OCT) apparatus according to claim 5, wherein
    the optical coherence tomography (OCT) apparatus is configured to perform:
        whether the object light is emitted onto the measurement object based on information caused by the object light scattered from the surface of the measurement object among the pieces of information on the change in the intensity ratio between the interference light beams generated by the irradiation optical system irradiating the object light.

7. The optical coherence tomography (OCT) apparatus according to claim 6, wherein
    the optical coherence tomography (OCT) apparatus is configured to perform:
        determining whether the object light is emitted onto the measurement object based on information caused by the object light scattered from a structure existing in the depth direction from the surface of the measurement object among the pieces of information related to the change in the intensity ratio between the interference light beams generated by the irradiation optical system irradiating the object light.

8. The optical coherence tomography (OCT) apparatus according to claim 6, wherein
    the optical coherence tomography (OCT) apparatus is configured to perform:
        determining whether the object light is emitted onto the measurement object in consideration of information caused by the object light scattered from a transparent member located between the irradiation optical system and the measurement object among the pieces of information related to the change in the intensity ratio between the interference light beams generated by the irradiation means irradiation optical system irradiating the object light.

9. A method for controlling an optical coherence tomography (OCT) apparatus, the optical coherence tomography (OCT) apparatus including:
- a wavelength-swept laser light source; an optical branching device configured to branch light emitted from the wavelength-swept laser light source into object light and reference light; and
- an irradiation optical system configured to irradiate different positions on a surface of a measurement object with the object light output from the optical branching device to scan a predetermined range, the method comprising:
- generating information on a change in an intensity ratio between interference light beams generated from the object light emitted to the measurement object and then scattered from the measurement object and the reference light, acquiring structure data in a depth direction of the measurement object, based on the information on the change in the intensity ratio between the interference light beams,
- determining whether the measurement object is irradiated with the object light based on the generated information, and
- setting an irradiation position of the object light controlled by the irradiation optical system.

10. The method for controlling an optical coherence tomography (OCT) apparatus according to claim 9, further comprising
- setting a center of an irradiatable range as a start point with respect to initial setting of an irradiation position of the object light with respect to the measurement object.

11. The method for controlling an optical coherence tomography (OCT) apparatus according to claim 9, further comprising
- changing the irradiation position of the object light in a direction substantially perpendicular to a scanning direction of the object light when an end point of the scanning direction of the object light is detected.

12. The method for controlling an optical coherence tomography (OCT) apparatus according to claim 9, further comprising
- determining an end point in the scanning direction of the object light, by determining whether the object light is emitted onto the measurement object based on the information on the change in the intensity ratio between the interference light beams generated by the irradiation optical system irradiating the object light.

* * * * *